United States Patent
Fugoso et al.

[11] Patent Number: 5,964,778
[45] Date of Patent: Oct. 12, 1999

[54] BALLOON ATTACHMENT AT CATHETER TIP

[75] Inventors: Mauricio L. Fugoso, Chula Vista; Karen M. Rowean, San Diego; Michelle E. Fourmont, Carlsbad; Christopher Todd Brahana, San Diego; Sharon Ma Schwab, San Diego; Maritess E. Minas, San Diego, all of Calif.

[73] Assignee: Medtronic, Inc., Minneapolis, Minn.

[21] Appl. No.: 09/040,505

[22] Filed: Mar. 17, 1998

[51] Int. Cl.⁶ ...................................... A61M 29/00
[52] U.S. Cl. .............................. 606/194; 604/96
[58] Field of Search .................... 606/191, 194, 606/198, 195; 604/96–101

[56] References Cited

U.S. PATENT DOCUMENTS

| | | |
|---|---|---|
| 4,003,382 | 1/1977 | Dyke . |
| 4,543,087 | 9/1985 | Sommercorn et al. . |
| 4,588,398 | 5/1986 | Daugherty et al. . |
| 4,661,300 | 4/1987 | Daugherty . |
| 4,702,252 | 10/1987 | Brooks et al. . |
| 4,739,768 | 4/1988 | Engelson . |
| 4,787,388 | 11/1988 | Hofmann . |
| 4,798,586 | 1/1989 | Stevens . |
| 4,820,349 | 4/1989 | Saab . |
| 4,877,031 | 10/1989 | Conway et al. . |
| 4,921,483 | 5/1990 | Wijay et al. . |
| 5,047,045 | 9/1991 | Arney et al. . |
| 5,195,969 | 3/1993 | Wang et al. . |
| 5,209,728 | 5/1993 | Kraus et al. . |
| 5,209,799 | 5/1993 | Vigil . |
| 5,290,230 | 3/1994 | Ainsworth et al. . |
| 5,304,134 | 4/1994 | Kraus et al. . |
| 5,320,634 | 6/1994 | Vigil et al. . |
| 5,338,295 | 8/1994 | Cornelius et al. . |
| 5,344,401 | 9/1994 | Radisch et al. . |
| 5,344,402 | 9/1994 | Crocker . |

(List continued on next page.)

FOREIGN PATENT DOCUMENTS

| | | |
|---|---|---|
| 0 184 314 | 6/1986 | European Pat. Off. . |
| 0 408 198 A1 | 1/1991 | European Pat. Off. . |
| 0 597 465 A1 | 5/1994 | European Pat. Off. . |
| WO 96/09848 | 4/1996 | WIPO . |

OTHER PUBLICATIONS

GUIDANT Advanced Cardiovascular Systems, Inc. Brochure, ACS RX ROCKET™ Coronary Dilatation Catheter with XCELON™ Balloon Material–Cross to a New World, Mar. 24, 1997, Temecula, California, USA.

Schneider (Europe) AG—Pfizer Hospital Products Group Brochure, The Magical Speedy™ 2.4F MONORAIL™ PCTA Balloon Catheter, Aug., 1993, Bülach, Switzerland.

Schneider USA, Inc.—A Pfizer Company® Brochure, MYSTIC™ Over–the–Wire PTCA Balloon Catheter—At One With the Elements, Minneapolis, Minnesota, USA. The product illustrated in this brochure is currently believed to have been on sale more than one (1)year ago.

(List continued on next page.)

*Primary Examiner*—Michael Buiz
*Assistant Examiner*—William W. Lewis
*Attorney, Agent, or Firm*—Steven G. Roeder; Dianne Plunkett Latham; Harold R. Patton

[57] ABSTRACT

An intravascular medical catheter and method of manufacturing a medical catheter are provided herein. The medical catheter includes a guidewire shaft, a sleeve, and a balloon. The sleeve is attached to the guidewire shaft while a distal tail of the balloon is thermally bonded to the sleeve. Because of the sleeve, the distal tail of the balloon can be thermally bonded even if the guidewire shaft is made of a material which is thermally incompatible with the balloon. Thus, for example, a medical catheter can be made with an HDPE guidewire shaft and a balloon made of PEBA, PET, Polyurethane, or Nylon. The resulting medical catheter has a catheter tip which is durable, flexible, and has a relatively low profile for good tracking in the body vessel and good lesion crossing.

26 Claims, 4 Drawing Sheets

U.S. PATENT DOCUMENTS

| | | |
|---|---|---|
| 5,366,442 | 11/1994 | Wang et al. . |
| 5,370,615 | 12/1994 | Johnson . |
| 5,382,234 | 1/1995 | Cornelius et al. . |
| 5,411,016 | 5/1995 | Kume et al. . |
| 5,423,745 | 6/1995 | Todd et al. . |
| 5,423,771 | 6/1995 | Imran . |
| 5,425,712 | 6/1995 | Goodin . |
| 5,569,196 | 10/1996 | Muni et al. . |
| 5,643,209 | 7/1997 | Fugoso et al. . |
| B1 4,739,768 | 11/1994 | Engelson . |

OTHER PUBLICATIONS

Schneider USA, Inc.—A Pfizer Company® Brochure, Monorail PICCOLINO™ Percutaneous Transluminal Coronary Angioplasty (PTCA) Catheter, Jul., 1989, Minneapolis, Minnesota, USA.

Schneider USA, Inc.—A Pfizer Company® Brochure, MICROSOFTRAC® Percutaneous Transluminal Coronary Angioplasty (PTCA) Catheter, Jun., 1989, Minneapolis, Minnesota, USA.

Schneider (Europe) AG—Pfizer Hospital Products Group Brochure GOLDIE™ 2.4F Monorail™ PTCA Balloon Catheter, Bülach, Switzerland. The product illustrated in this brochure is currently believed to have been on sale more than one (1) year ago.

Schneider (USA) Inc.—Pfizer Hospital Products Group Brochure, SHORTGOOSE™ NC Non–Compliant, High Pressure PTCA Catheter, 1994, Minneapolis, Minnesota, USA.

Schneider (USA) Inc.—Pfizer Hospital Products Group Brochure, FREEHAND™ PTCA Balloon Catheter: FREEHAND™ Dual–Tapered TracTip™, 1993, Minneapolis, Minnesota, USA.

Schneider (USA) Inc.—Pfizer Hospital Products Group Brochure, MONGOOSE™ PCTA Balloon Catheter, 1992, Minneapolis, Minnesota, USA.

Cordis® Corporation Brochure, TRAKSTAR™ PTCA Balloon Catheter—The First to Cross!, Aug., 1994, Miami, Florida, USA.

Cordis® Corporation Brochure, TITAN™18 PTCA Dilatation Catheter, Miami, Florida, USA. The product illustrated in this brochure is currently believed to have been on sale more than one (1) year ago.

Application for United States Letters Patent for Catheter Distal Tip Component by Sharon Schwab and Maritess E. Minas, filed on Apr. 24, 1997, Application No. 08/839,998.

Application for United States Letters Patent for Catheter Flexible Distal Tip by Sharon Ma, filed on Sep. 26, 1994, Application No. 08/312,359.

Application for United States Letters Patent for High Pressure Balloon Tip by Mauricio Lintag Fugoso and Candida Naguit Figueroa, filed on Dec. 15, 1995, Application No. 08/572,908.

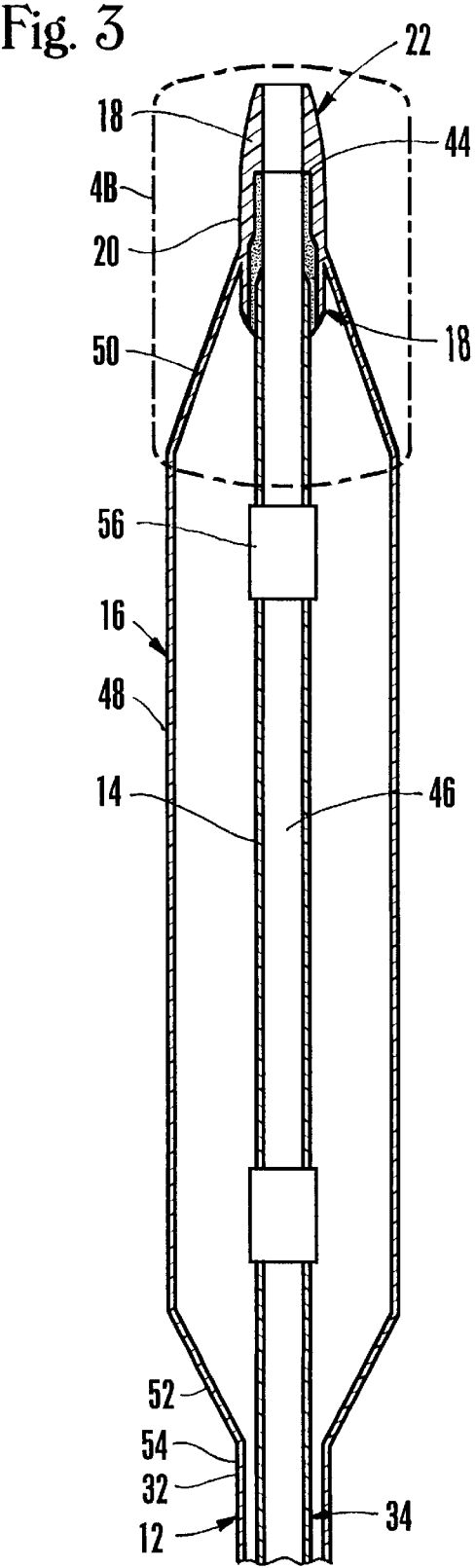
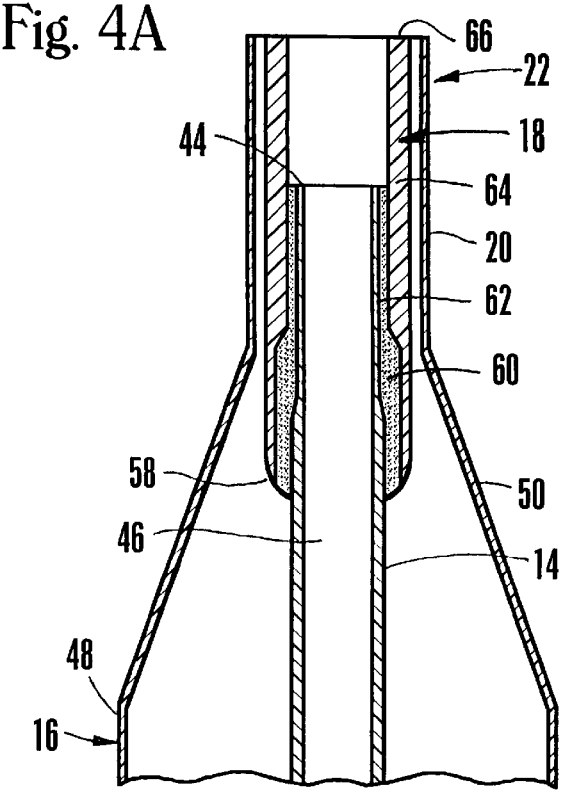
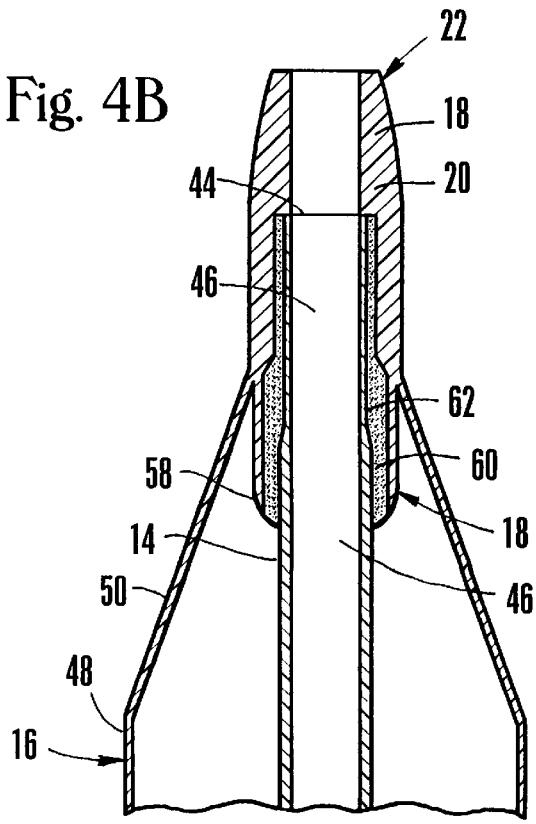

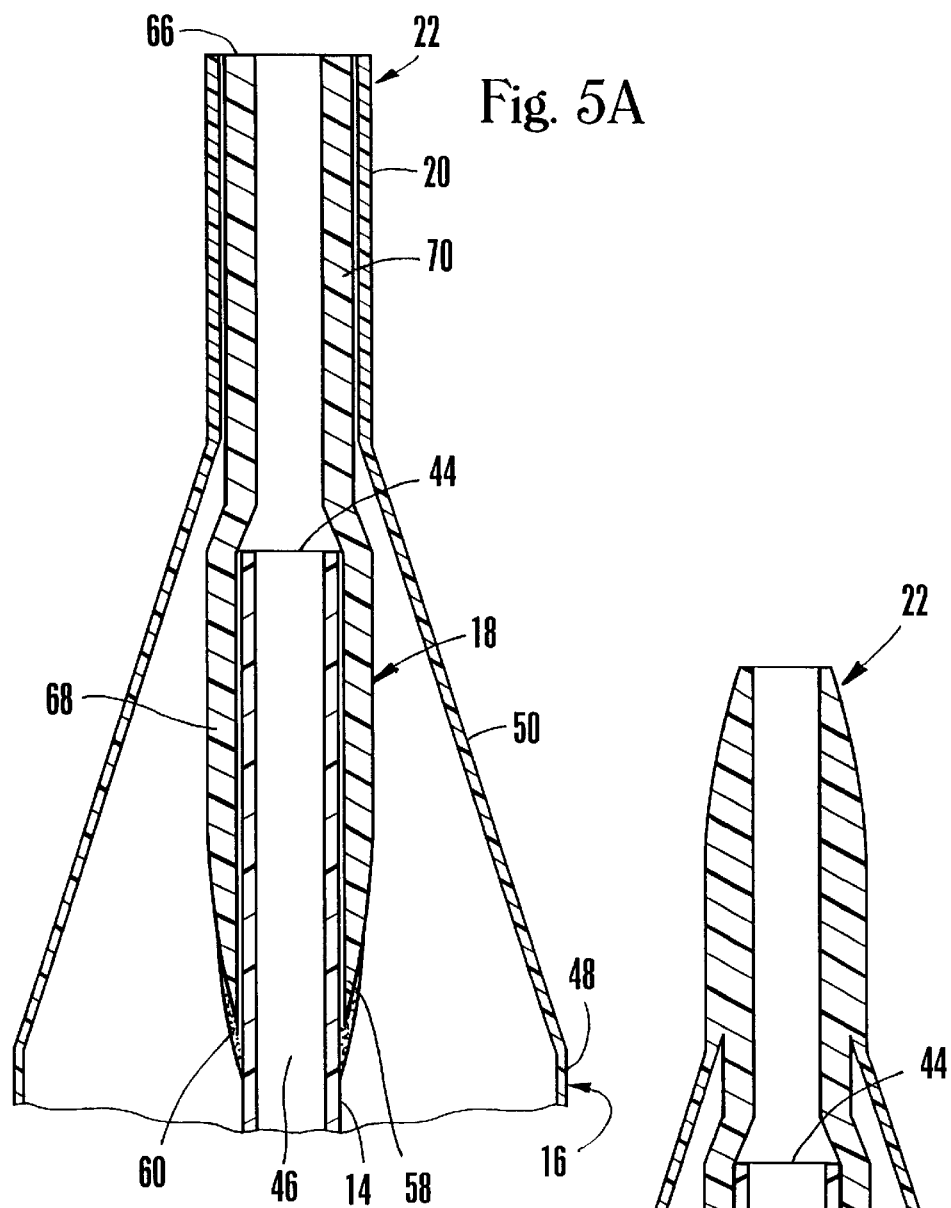
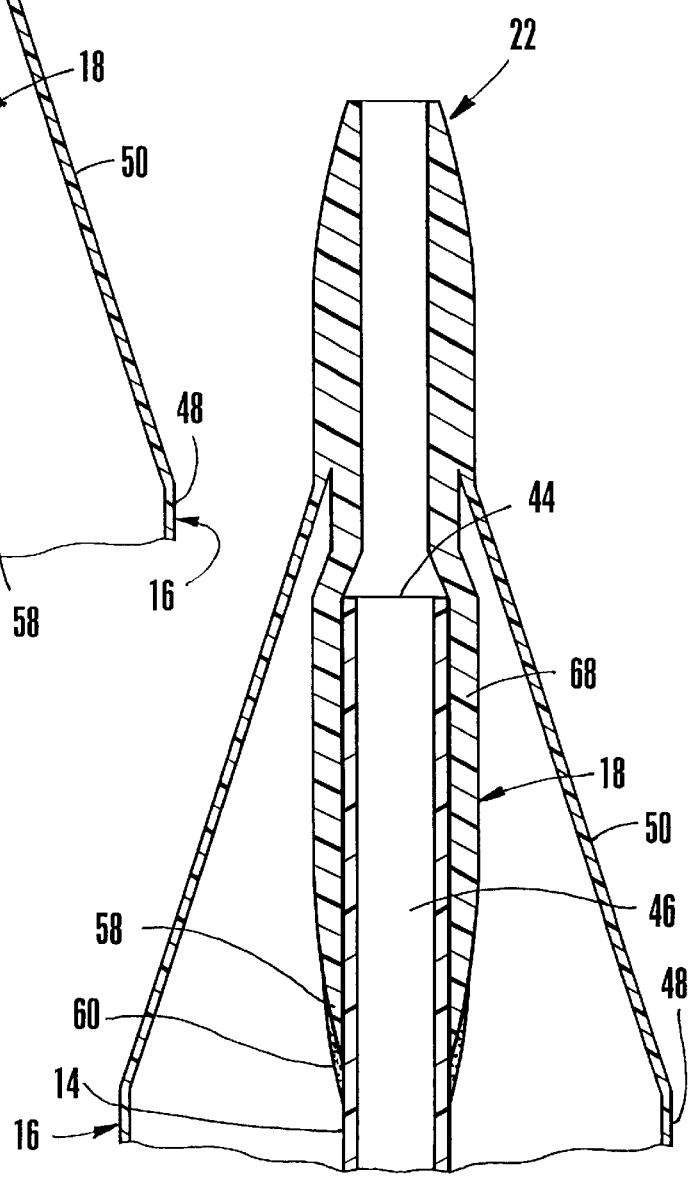

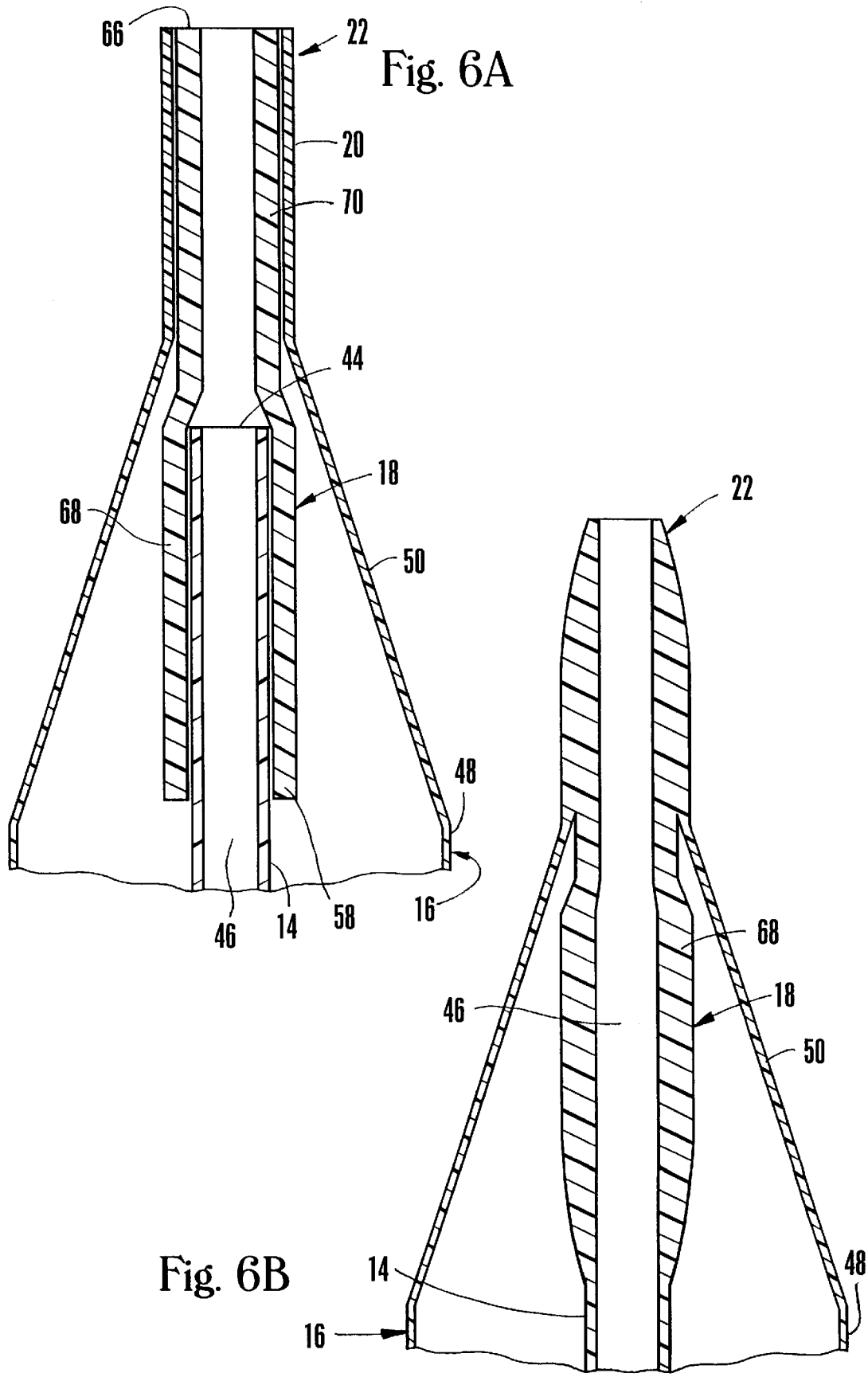

BALLOON ATTACHMENT AT CATHETER TIP

FIELD OF THE INVENTION

The present invention relates to an intravascular medical catheter and a method of manufacturing an intravascular medical catheter. More specifically, the present invention relates to a medical catheter having good guidewire movement and tracking, as well as good tip flexibility and durability.

BACKGROUND

Percutaneous transluminal coronary angioplasty (hereinafter "angioplasty") is a procedure used to treat a stenosis within a body vessel of a human being. A medical catheter having an inflatable balloon attached to a catheter shaft and a guidewire shaft is commonly used during the angioplasty procedure. First, the guidewire shaft and balloon are advanced over a guidewire which is positioned within the body vessel until the balloon is adjacent to the stenosis. Subsequently, the balloon is inflated. This causes the site of the stenosis to compress into the arterial wall and the body vessel to dilate.

In recent years, there has been a continuing effort to improve the performance characteristics of medical catheters. Unfortunately, the design of most existing medical catheters has always involved trading off various performance characteristics. For example, many physicians prefer the guidewire movement/tracking of a guidewire shaft made of high density polyethylene ("HDPE") instead of a guidewire shaft made of Polyether Block Amide ("PEBA"), Polyethylene Terephthalate ("PET"), or Nylon. However, a balloon made of HDPE, in many instances, may not have satisfactory inflation or pressure characteristics. In fact, for some applications, balloons made of PEBA, PET, or Nylon provide superior inflation and pressure characteristics. Because PEBA, PET, and Nylon can not be thermally bonded to HDPE, it is often necessary to use an adhesive to bond a PEBA, PET, or Nylon balloon to a HDPE guidewire shaft. Unfortunately, the adhesive bond at the catheter tip has a relatively large profile, and is relatively stiff. As a result thereof the medical catheter is relatively difficult to maneuver because the catheter tip does not track well in the body vessel.

One attempt to solve this problem involves utilizing the same or thermally compatible materials for the guidewire shaft and the balloon, so that the balloon can be thermally bonded to the guidewire shaft. The thermal bonding results in a high strength, durable, flexible, transitionless, and low profile catheter tip. For example, Guidant, located in Temecula, California, manufactures a medical catheter having a balloon and guidewire shaft which are made of nylon. However, this device is not entirely satisfactory because physicians typically prefer a guidewire shaft made of HDPE.

Another attempt to solve this problem involves the co-extrusion of the guidewire shaft with an inner tube made of HDPE and an outer shell made of nylon. Subsequently, a nylon balloon can be thermally bonded to the nylon outer shell. Unfortunately, the co-extruded guidewire shaft can be more difficult to manufacture and delamination of the co-extruded guidewire shaft may occur.

In light of the above, it is an object of the present invention to provide an improved medical catheter which utilizes a guidewire shaft made of HDPE regardless of the material utilized for the inflatable balloon. Another object of the present invention is to provide a medical catheter having good guidewire movement and tracking, as well as a catheter tip having a low profile, and good strength, flexibility and durability characteristics. Still another object of the present invention is to provide a medical catheter having a distal tail which is thermally bonded and transitionless.

SUMMARY

The present invention is directed to a medical catheter useful for an angioplasty procedure which satisfies these objectives. The medical catheter includes a guidewire shaft, a sleeve attached to the guidewire shaft, and an inflatable balloon having a distal tail which is thermally bonded to the sleeve. As provided in detail below, the thermal bonding of the distal tail of the balloon to the sleeve results in a high strength, low profile, flexible, and transitionless catheter tip. Further, because of this unique design, a guidewire shaft made of HDPE can be utilized regardless of the material utilized for the balloon. Therefore, the material utilized for the guidewire shaft and the material utilized for the inflatable balloon can be particularly tailored to suit the preferences of the physician.

As used herein, the term "thermal bonding" shall mean the bonding of two mated polymer materials, upon the application of heat. The term "thermally compatible" shall mean the condition where two mated polymer materials, upon the application of heat, bond together with no discernible interface, i.e., they are miscible. Polymers which are identical are thermally compatible. However, the polymers do not have to be identical to be thermally compatible. For example, a higher durometer material is thermally compatible to a lower durometer of the same material.

As used herein, the term "thermally incompatible" shall mean the condition where two mated polymer materials, upon the application of heat, form distinct phases at their interface and crystallize independently of each other.

Because of the sleeve, the catheter tip can be thermally bonded, even though the guidewire shaft is made of a guidewire shaft material which is not thermally compatible with a balloon material which is utilized for the balloon. For example, the guidewire shaft material can be a high density polyethylene ("HDPE") while the balloon material and the sleeve material can be PEBA, PET, Nylon, Polyurethane, or blends thereof. As the result of the thermal bond between the sleeve and the balloon, the balloon is easier to move in the body vessel, commonly referred to herein as "improved tracking." Further, the inflatable balloon is easier to move past the lesion in the vessel, commonly referred to as "improved lesion crossing characteristics." In one embodiment of the present invention, an adhesive is positioned between the guidewire shaft and the sleeve to sealingly affix the sleeve to the thermally incompatible guidewire shaft. In a second embodiment of the present invention, the sleeve is compression bonded to the thermally incompatible guidewire shaft. In the second embodiment, because the sleeve and the guidewire shaft are thermally incompatible, heating of the sleeve and guidewire shaft merely results in the sleeve being compressed against the guidewire shaft. In this embodiment, an adhesive can cover the proximal end of the sleeve and a portion of the guidewire shaft to inhibit peeling of the sleeve away from the guidewire shaft.

In a third embodiment, the guidewire shaft and sleeve are thermally compatible and the sleeve can be thermally bonded to the guidewire shaft. In this embodiment, the sleeve and guidewire shaft can be made of a polymer having a different durometer. For example, a lower durometer material can be used for the sleeve while a higher durometer of the same material can be used for the guidewire shaft. Therefore, the sleeve is more flexible than the guidewire shaft. The resulting medical catheter has a flexible catheter tip to enhance tracking and lesion crossing, and a guidewire shaft with appropriate column strength.

The present invention is also a method for making a medical catheter. The method includes providing a guidewire shaft, attaching a tubular sleeve to the guidewire shaft, and thermally bonding a distal tail of an inflatable balloon to the tubular sleeve. Utilizing this procedure, the distal tail of the balloon can be thermally bonded, even though the guidewire shaft and the inflatable balloon are made from thermally incompatible materials.

Importantly, the medical catheter provided herein has good guidewire movement and tracking, good vessel tracking and lesion crossing characteristics, and good tip strength and durability characteristics.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 3 is a cross-sectional view of a portion of one embodiment of the medical catheter;

FIG. 4A is an enlarged, cross-sectional assembly view of the medical catheter of FIG. 3;

FIG. 4B is an enlarged, cross-sectional view of the medical catheter taken from FIG. 3;

FIG. 5A is an enlarged, cross-sectional assembly view of a portion of a second embodiment of a medical catheter having features of the present invention;

FIG. 5B is an enlarged, cross-sectional view of a portion of the medical catheter of FIG. 5A;

FIG. 6A is an enlarged, cross-sectional assembly view of a portion of a third embodiment of a medical catheter having features of the present invention; and FIG. 6B is an enlarged, cross-sectional view of a portion of the medical catheter of FIG. 6A.

DESCRIPTION

Figure 1:
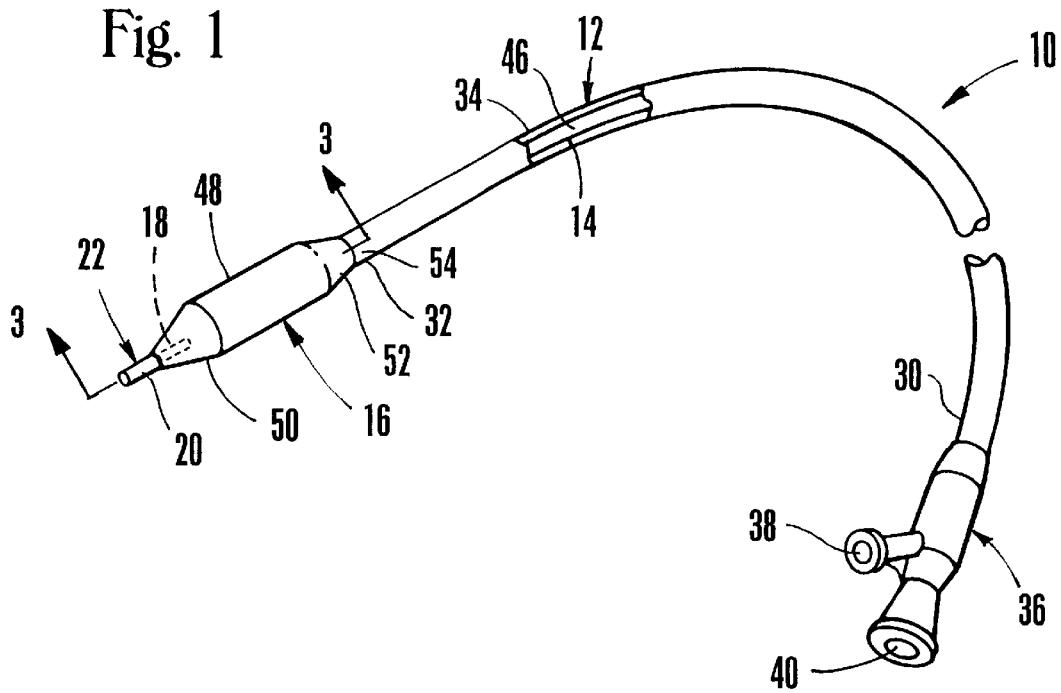
FIG. 1 is a perspective view, in partial cutaway, of a medical catheter having features of the present invention.

Referring to FIG. 1, a medical catheter 10 having features of the present invention includes a catheter shaft 12, a guidewire shaft 14, an inflatable balloon 16, and a tubular sleeve 18 (shown in phantom in FIG. 1). As provided in detail below, the tubular sleeve 18 fits over a portion of the guidewire shaft 14 and is thermally bonded to a distal tail 20 of the inflatable balloon 16. Because the balloon 16 is thermally bonded to the sleeve 18 instead of bonded with an adhesive 60 to the guidewire shaft 14, a tip 22 of the medical catheter 10 has a lower profile and better strength, durability, and flexibility characteristics. Further, because of the sleeve 18, the medical catheter 10 can utilize a guidewire shaft 14 made of HDPE for preferred movement and tracking over a guidewire 24 (shown in FIG. 2) with a thermally incompatible balloon 16.

Figure 2:
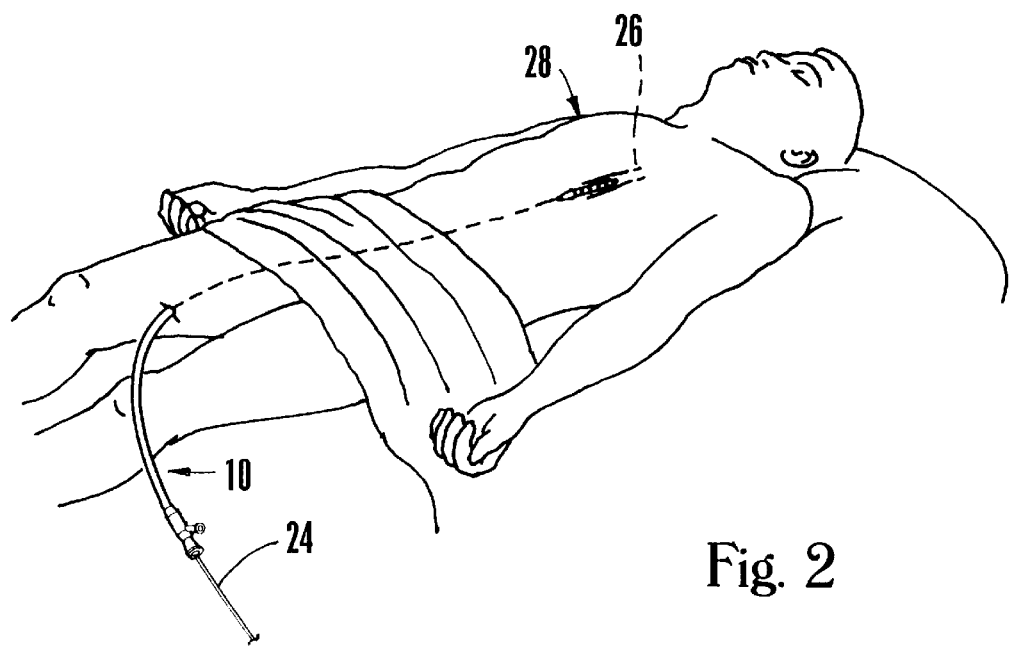
FIG. 2 is a perspective view of the medical catheter positioned within a patient.

As illustrated in FIG. 2, a portion of the medical catheter 10 and the guidewire 24 can be positioned in a body vessel 26 of a patient 28 during an angioplasty procedure. The location of entry into the patient 28 and the location of the inflatable balloon 16 illustrated in FIG. 2 is merely exemplary.

The catheter shaft 12 is used by the physician to position the inflatable balloon 16 within the body vessel 26 and transfer an inflation fluid (not shown) to the inflatable balloon 16. In the embodiment shown in FIG. 1, the catheter shaft 12 includes a catheter shaft proximal end 30, a catheter shaft distal end 32, and an inflation lumen 34 in fluid communication with the balloon 16. A manifold 36 having an inflation/deflation port 38 and a guidewire port 40 is secured to the catheter shaft proximal end 30. The inflation/deflation port 38 is in fluid communication with the inflation lumen 34 while the guidewire port 40 is connected to the guidewire shaft 14. In the embodiments illustrated in the Figures, the inflatable balloon 16 is secured to the catheter shaft distal end 32. Further, the catheter shaft 12 encircles and is substantially coaxial with the guidewire shaft 14.

Preferably, the catheter shaft 12 is made of a material which is thermally compatible with the balloon 16 so that the balloon 16 can be thermally bonded to the catheter shaft 12. For example, the catheter shaft 12 can be manufactured by extruding a polymer such as PEBA, PET, Polyurethane, PE, or Nylon.

The guidewire shaft 14 includes a guidewire shaft proximal end (not shown), a guidewire shaft distal end 44 (shown in FIGS. 3–5), and a guidewire lumen 46. The guidewire shaft proximal end is connected to the guidewire port 40, while the guidewire shaft distal end 44 is attached to the tubular sleeve 18. The guidewire lumen 46 is sized and shaped to receive the guidewire 24. A guidewire shaft 14 having a 0.017 inch inner diameter and a 0.023 inch outer diameter is suitable for a standard 0.14 inch guidewire 24.

Typically, the guidewire shaft 14 is made by extruding a guidewire shaft material. Presently, the preferred guidewire shaft material is High Density Polyethylene ("HDPE") which provides excellent movement and tracking of the guidewire shaft 14 over the guidewire 24. Alternately, for example, a Low Density Polyethylene ("LDPE") with an additive, or an HDPE/LDPE blend can be utilized for the guidewire shaft 14.

The balloon 16 can be used to dilate the body vessel 26 and/or position a stent (not shown) within the body vessel 26. The balloon 16 includes a body section 48 which separates a distal cone section 50 from a proximal cone section 52. Prior to assembly, the inflatable balloon 16 includes a proximal tail 54 which can be thermally bonded to the catheter shaft 12 and the distal tail 20 which is thermally bonded to the sleeve 18. Alternately, the proximal tail 54 can be bonded with an adhesive to the catheter shaft 12. Typically, the balloon size for use in a body vessel 26 ranges from between approximately five millimeters to fifty millimeters (5 mm–50 mm) in length and between approximately one and one-half millimeters to five millimeters (1.5 mm–5.0 mm) in diameter.

The balloon 16 can be manufactured by initially extruding a balloon material to form a tube. Subsequently, the tube is heated above its glass transition temperature and radially expanded within a blow mold (not shown) to form the balloon 16. Preferred balloon materials include PEBA, PET, PE, Polyurethane, Nylon, or blends thereof because balloons made from these materials have excellent inflation and rewrap characteristics. It is important to note that PEBA, PET, Polyurethane, and Nylon are thermally incompatible with HDPE.

The tubular sleeve 18 sealingly attaches to the guidewire shaft 14 and sealingly attaches the distal tail 20 to the guidewire shaft 14. Preferably, the sleeve 18 is made of a sleeve material which is thermally compatible with the balloon material so that the sleeve 18 can be thermally bonded to the distal tail 20 of the balloon 16. For example, the tubular sleeve 18 can be manufactured by extruding a polymer such as PEBA, PET, PE, Polyurethane, Nylon, or blends thereof. The sleeve material is also chosen based upon the desired catheter tip 22 stiffness and strength. The sleeve material should be thermally compatible to the balloon material and does not have to be identical to the balloon material.

With the teaching provided herein, those skilled in the art will recognize alternate ways to manufacture the catheter shaft 12, the guidewire shaft 14, the balloon 16, and the sleeve 18 and that alternate materials can be utilized for these components.

A cross-sectional view of a portion of a first embodiment of the medical catheter 10 is illustrated in FIG. 3. In this embodiment, the proximal tail 54 of the balloon 16 is thermally bonded to the catheter shaft 12. Further, a pair of spaced apart, tubular, radiopaque markers 56 can be bonded to the guidewire shaft 14 to facilitate proper positioning of the inflatable balloon 16 in the body vessel 26.

FIGS. 4A and 4B each illustrate an enlarged view of the catheter tip 22 of the embodiment shown in FIG. 3. More specifically, FIG. 4A shows the catheter tip 22 during assembly, prior to thermal bonding, while FIG. 4B shows the catheter tip 22 after thermal bonding. In this embodiment, a sleeve proximal end 58 is attached with an adhesive 60 to the guidewire shaft distal end 44. The adhesive 60 is positioned between the sleeve 18 and the guidewire shaft 14 to sealingly attach the sleeve 18 to the guidewire shaft 14. A suitable adhesive 60 is sold under the trade name Loctite® 3311 U.V. by Loctite® Corporation located in Hartford, Conn. Suitable alternate adhesives include Loctite® 3321 U.V. and Loctite® 420 Cyanoacrylate sold by Loctite® Corporation or UR-0531 Urethane adhesive sold by H. B. Fuller located in St. Paul, Minn.

With reference to FIG. 4A, an outer diameter of the guidewire shaft 14 includes a necked down section 62 proximal to the guidewire shaft distal end 44 and an inner surface of the sleeve 18 includes a corresponding thick walled section 64. The necked down section 62 of the guidewire shaft 14 has a smaller outer diameter than the rest of the guidewire shaft 14 while the thick walled section 64 has a smaller inner diameter than the rest of the sleeve 18. This allows the thick walled section 64 to be attached to the distal tail 54 while minimizing the profile of the catheter tip 22.

In the embodiment shown in FIG. 4A, the sleeve 18 encircles only between approximately one-half millimeter (0.5 mm) and fifteen millimeters (15 mm) of the guidewire shaft 14 and more preferably between one-half millimeter (0.5 mm) to two millimeters (2.0 mm), to minimize the profile of the medical catheter 12 and stiffness related to the bond. Preferably, a sleeve distal end 66 extends past the guidewire shaft distal end 44 to minimize the profile of the medical catheter 10 and stiffness at the catheter tip 22 related to the bond. For example, the sleeve distal end 66 can extend past the guidewire shaft distal end 44 between approximately one-half millimeter (0.5 mm) and five millimeters (5.0 mm). Alternately, the sleeve distal end 66 can be substantially even with the guidewire shaft distal end 44. If the sleeve 18 extends past the guidewire shaft 14, the sleeve distal end 66 can be formed to have substantially the same inner diameter as the guidewire lumen 46 during thermal bonding to the distal tail 20 of the balloon 16.

FIG. 4B illustrates the sleeve distal end 66 attached to the distal tail 20 of the balloon 16 with thermal bonding. The thermal bond causes the sleeve 18 and the distal tail 20 to appear as a single, unitary component. The resulting thermal bond is relatively strong, transitionless, flexible, and durable. Additionally, the thermal bond has a low profile for improved tracking and lesion crossing in the vessel 26. Further, the catheter tip 22 can be tapered for improved tracking and lesion crossing.

FIGS. 5A and 5B each illustrate an enlarged view of a second embodiment of the catheter tip 22. More specifically, FIG. 5A shows the catheter tip 22 prior to thermal bonding, while FIG. 5B shows the catheter tip 22 after thermal bonding between the sleeve 18 and the balloon 16. In this embodiment, if the sleeve 18 and the guidewire shaft 14 are thermally incompatible, the tubular sleeve 18 can be compression bonded to the guidewire shaft 14. Further, an adhesive 60 can cover a portion of the guidewire shaft 14 and an outer surface of the sleeve proximal end 58 to prevent peeling of the sleeve 18 from the guidewire shaft 14. Suitable adhesives 60 include Loctite® 420 Cyanoacrylate, Loctite® 3311, or Loctite® 3321 sold by Loctite® Corporation, or U.R.-0531 sold by H. B. Fuller located in St. Paul, Minn.

Referring back to FIG. 5A, the sleeve 18 can include a sleeve shaft section 68 which encircles the guidewire shaft 14 and a sleeve tail section 70 which fits within the distal tail 20 of the balloon 16. In this embodiment, the inner diameter of sleeve shaft section 68 is larger than the inner diameter of the sleeve tail section 70. This allows the sleeve shaft section 68 to fit over the guidewire shaft 14 while the sleeve tail section 70 has substantially the same inner diameter as the guidewire lumen 46. The sleeve shaft section 68 encircles between approximately one millimeter (1.0 mm) and fifteen millimeters (15 mm) of the guidewire shaft 14, and more preferably between two millimeters (2.0 mm) to three millimeters (3.0 mm) to minimize the profile and stiffness related to bond. Preferably, the sleeve distal end 66 extends past the guidewire shaft distal end 44 to minimize the profile of the medical catheter 10 and stiffness at the catheter tip 22 related to the bond. For example, the sleeve distal end 66 can extend past the guidewire shaft distal end 44 between approximately one-half millimeter (0.5 mm) and five millimeters (5.0 mm). Alternately, the sleeve distal end 66 can be substantially even with the guidewire shaft distal end 44. If the sleeve 18 extends past the guidewire shaft 14, the sleeve distal end 66 can be formed to have substantially the same inner diameter as the guidewire lumen 46 during thermal bonding to the distal tail 20 of the balloon 16.

Referring to FIG. 5B, the thermal bonding causes the tubular sleeve 18 and the distal tail 20 to appear as a single, homogenous component. The resulting thermal bond is relatively strong, transitionless, durable, and flexible and has a low profile to allow for improved tracking and lesion crossing. Further, as shown in FIG. 5B, the sleeve 18 merely contacts the guidewire shaft 14 as a result of the compression bond. Additionally, the catheter tip 22 can be tapered for improved tracking and lesion crossing.

FIGS. 6A and 6B each illustrate an enlarged view of a third embodiment of the catheter tip 22. FIG. 6A shows the catheter tip 22 prior to thermal bonding, while FIG. 6B shows a catheter tip 22 after thermal bonding of the guidewire shaft 14 to the sleeve 18, and the sleeve 18 to the balloon 16. In this embodiment, the guidewire shaft 14, the sleeve 18, and the balloon 16 are all thermally compatible. Even though the balloon 16 and the guidewire shaft 14 are thermally compatible, it is desirable in many instances, to utilize a sleeve 18 which is more flexible than the guidewire shaft 14. This embodiment is particularly useful for joining a sleeve 18 made of a lower durometer material to a guidewire shaft 14 made of a higher durometer of the same material. For example, the guidewire shaft 14 could be made out of a high density HDPE, while the sleeve 18 is made from a LDPE which is more flexible. Another example would be a guidewire shaft 14 made of Pebax® 7233 and a sleeve 18 made of Pebax® 7033. Pebax® is a PEBA sold by Elf Atochem North America, located in Philadelphia, Pa. In either example, the resulting medical catheter 10 has a more flexible catheter tip 22 for improved tracking and lesion crossing. Further, because the guidewire shaft 14 is thermally bonded to the sleeve 18 and the sleeve 18 is thermally bonded to the balloon 16, the catheter tip 22 is transition less.

In the embodiment shown in FIG. 6A, prior to thermal bonding, the sleeve 18 includes the sleeve shaft section 68 which encircles the guidewire shaft 14 and the sleeve tail section 70 which fits within the distal tail 20 of the balloon 16. After assembly, as illustrated in FIG. 6B, thermal bonding causes the guidewire shaft 14, the tubular sleeve 18, and the distal tail 20 to appear as a single, homogeneous component. The resulting thermal bond is relatively strong, transitionless, durable, flexible, and has a profile for improved tracking and lesion crossing. Additionally, in this embodiment, the catheter tip 22 can be tapered for improved tracking and lesion crossing.

Importantly, the thermal bonding of the distal tail 20 to the tubular sleeve 18 allows the medical catheter 10 provided herein to have a low profile. This results in improved tracking and lesion crossing characteristics. Further, the thermal bond is stronger, more durable, and more flexible than an adhesive bond. Additionally, because of the unique design provided herein, the medical catheter 10 can utilize a HDPE guidewire shaft 14 for preferred guidewire 24 movement and tracking with a thermally incompatible balloon material.

While the particular medical catheter 10 as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A medical catheter adapted for use within a body vessel with a guidewire, the medical catheter comprising:
    a guidewire shaft having a guidewire lumen which is adapted to receive the guidewire;
    a sleeve attached to the guidewire shaft after extrusion of the guidewire shaft; and
    an inflatable balloon having a distal tail which is thermally bonded to the sleeve to attach the distal tail of the balloon to the sleeve;
    wherein the balloon includes a distal cone section which encircles both a portion of the quidewire shaft and a portion of the sleeve.

2. The medical catheter of claim 1 wherein the sleeve is tubular and encircles only a portion of the guidewire shaft.

3. The medical catheter of claim 1 wherein the sleeve includes a sleeve distal end which extends past a guidewire shaft distal end of the guidewire shaft.

4. The medical catheter of claim 1 wherein the guidewire shaft is made of a guidewire shaft material which is thermally incompatible with a balloon material which is utilized in the balloon.

5. The medical catheter of claim 4 wherein the sleeve is made of a sleeve material which is thermally compatible with the balloon material and thermally incompatible with the guidewire shaft material.

6. The medical catheter of claim 5 wherein the balloon material is selected from a group consisting of PEBA, PET, Polyurethane, and Nylon and the sleeve material is selected from a group consisting of PEBA, PET, Polyurethane, and Nylon.

7. The medical catheter of claim 4 wherein the guidewire shaft material includes polyethylene.

8. The medical catheter of claim 1 wherein the sleeve is compression bonded to the guidewire shaft.

9. The medical catheter of claim 8 including an adhesive which covers a sleeve proximal end of the sleeve and a portion of the guidewire shaft to inhibit peeling of the sleeve away from the guidewire shaft.

10. The medical catheter of claim 1 including an adhesive for attaching the sleeve to the guidewire shaft.

11. The medical catheter of claim 10 wherein the adhesive is positioned between the guidewire shaft and the sleeve.

12. The medical catheter of claim 1 wherein the sleeve is thermally bonded to the guidewire shaft and the sleeve is made of a sleeve material which is thermally compatible with the quidewire shaft.

13. A medical catheter adapted for use within a body vessel with a guidewire, the medical catheter comprising:
    a guidewire shaft defining a guidewire lumen which is adapted to receive the guidewire, the guidewire shaft including a guidewire shaft distal end;
    a catheter shaft defining an inflation lumen, the catheter shaft encircling a portion of the guidewire shaft;
    a tubular sleeve which encircles only a portion of the guidewire shaft, the tubular sleeve being sealingly affixed to the guidewire shaft, the tubular sleeve being made of a sleeve material; and
    an inflatable balloon made of a balloon material which is thermally compatible with sleeve material, the inflatable balloon having a proximal tail which is bonded and sealingly affixed to the catheter shaft and a distal tail which is thermally bonded and sealingly affixed to the tubular sleeve.

14. The medical catheter of claim 13 wherein the guidewire shaft is made of a guidewire shaft material which is thermally incompatible with the balloon material which is utilized in the balloon and the sleeve material which is utilized in the sleeve.

15. The medical catheter of claim 14 wherein the guidewire shaft material includes polyethylene.

16. The medical catheter of claim 15 wherein the balloon material is selected from a group consisting of PEBA, PET, Polyurethane, and Nylon and the sleeve material is selected from a group consisting of PEBA, PET, Polyurethane, and Nylon.

17. The medical catheter of claim 13 wherein the sleeve is compression bonded to the guidewire shaft and includes an adhesive which covers a portion of an outer surface of the sleeve and a portion of the guidewire shaft to inhibit peeling of the sleeve away from the guidewire shaft.

18. The medical catheter of claim 13 including an adhesive positioned between the guidewire shaft and the sleeve to sealingly affix the sleeve to the guidewire shaft.

19. The medical catheter of claim 13 wherein the sleeve is thermally bonded to the guidewire shaft.

20. The medical catheter of claim 13 wherein the balloon includes a distal cone section which encircles both a portion of the guidewire shaft and a portion of the sleeve.

21. A medical catheter adapted for use within a body vessel with a guidewire, the medical catheter comprising:
   a guidewire shaft having a guidewire lumen which is adapted to receive the guidewire;
   a sleeve attached to the guidewire shaft after extrusion of the guidewire shaft, the shaft being made of a sleeve material; and
   an inflatable balloon made of a balloon material which is thermally compatible with the sleeve material, the inflatable balloon having a distal tail which is thermally bonded to the sleeve to attach the distal tail of the balloon to the sleeve.

22. A method for manufacturing a medical catheter which is adapted to be inserted within a body vessel, the method comprising the steps of:
   providing a guidewire shaft having a guidewire lumen which is adapted to receive a guidewire;
   providing a catheter shaft which encircles a portion of the guidewire shaft;
   attaching a tubular sleeve to the guidewire shaft, the tubular sleeve encircling only a portion of the guidewire shaft;
   bonding a proximal tail of an inflatable balloon to the catheter shaft to sealingly affix the proximal tail to the catheter shaft; and
   thermally bonding a distal tail of the inflatable balloon to the tubular sleeve to sealingly affix the distal tail to the sleeve.

23. The method of claim 22 wherein the step of providing a guidewire shaft includes providing a guidewire shaft made of a guidewire shaft material which is thermally incompatible with a balloon material which is utilized in the balloon and a sleeve material which is utilized in the sleeve.

24. The method of claim 22 wherein the step of attaching a tubular sleeve includes the steps of compression bonding the tubular sleeve to the guidewire shaft and applying an adhesive over a portion of an outer surface of the sleeve and a portion of the guidewire shaft to inhibit peeling of the sleeve away from the guidewire shaft.

25. The method of claim 22 wherein the step of attaching a tubular sleeve includes the step of applying an adhesive between the guidewire shaft and the sleeve to attach the sleeve to the guidewire shaft.

26. The method of claim 22 wherein the step of attaching a tubular sleeve includes the step of thermally bonding the tubular sleeve to the guidewire shaft.

* * * * *